United States Patent
Childers et al.

(10) Patent No.: US 10,429,542 B2
(45) Date of Patent: Oct. 1, 2019

(54) DEPTH CORRECTION BASED ON OPTICAL PATH MEASUREMENTS

(71) Applicants: Brooks A Childers, Christiansburg, VA (US); Christopher J Fazio, Blacksburg, VA (US); Roger Glen Duncan, Christiansburg, VA (US)

(72) Inventors: Brooks A Childers, Christiansburg, VA (US); Christopher J Fazio, Blacksburg, VA (US); Roger Glen Duncan, Christiansburg, VA (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 506 days.

(21) Appl. No.: 14/138,972

(22) Filed: Dec. 23, 2013

(65) Prior Publication Data

US 2015/0177411 A1    Jun. 25, 2015

(51) Int. Cl.
*G01V 8/16*        (2006.01)
*G01L 1/24*        (2006.01)
*G01V 8/00*        (2006.01)
*G01V 8/12*        (2006.01)
*G01V 8/10*        (2006.01)
*G02B 6/02*        (2006.01)
*E21B 47/06*       (2012.01)
*G01K 11/32*       (2006.01)
*G01J 3/10*        (2006.01)
*E21B 47/12*       (2012.01)
*G01D 5/353*       (2006.01)
*G01L 11/02*       (2006.01)
*E21B 47/09*       (2012.01)

(52) U.S. Cl.
CPC ............... *G01V 8/16* (2013.01); *E21B 47/06* (2013.01); *E21B 47/123* (2013.01); *G01D 5/35316* (2013.01); *G01J 3/10* (2013.01); *G01K 11/3206* (2013.01); *G01L 1/246* (2013.01); *G01L 11/025* (2013.01); *G01V 8/00* (2013.01); *G01V 8/10* (2013.01); *G01V 8/12* (2013.01); *G02B 6/02* (2013.01); *G02B 6/02076* (2013.01); *G02B 6/02347* (2013.01); *E21B 47/09* (2013.01); *G01K 2011/322* (2013.01); *G01N 2201/088* (2013.01); *G01N 2201/0886* (2013.01); *G02B 6/02057* (2013.01)

(58) Field of Classification Search
CPC ...................................................... G01V 8/16
See application file for complete search history.

(56) References Cited

U.S. PATENT DOCUMENTS 5,757,487 A * 5/1998 Kersey .......................... 356/478
5,844,927 A * 12/1998 Kringlebotn ..................... 372/6
(Continued)

Primary Examiner — Yara B Green
(74) Attorney, Agent, or Firm — Cantor Colburn LLP

(57) ABSTRACT

A method for estimating an environmental parameter includes transmitting a first interrogation signal into an optical fiber, receiving a reflected return signal including light reflected from one or more of the plurality of FBG's in the fiber and receiving at a processor data describing the reflected return signal. The received data is comparted to expected data to determine a shift in wavelength of light reflected for one or more of the plurality of FBGs and a change in a length of a dead zone of the optical fiber based on the comparison is also determined. From this, estimates of locations two or more of the plurality of FBG's are formed.

18 Claims, 5 Drawing Sheets

(56) References Cited

U.S. PATENT DOCUMENTS

| | | | |
|---|---|---|---|
| 6,072,567 A * | 6/2000 | Sapack | 356/32 |
| 6,915,040 B2 * | 7/2005 | Willner et al. | 385/37 |
| 2007/0065007 A1 * | 3/2007 | Yamazoe et al. | 382/167 |
| 2008/0232425 A1 * | 9/2008 | Hall et al. | 374/1 |
| 2009/0185772 A1 * | 7/2009 | Xia et al. | 385/13 |
| 2011/0110621 A1 * | 5/2011 | Duncan et al. | 385/13 |
| 2012/0237205 A1 * | 9/2012 | Duncan | E21B 47/0006 398/25 |

* cited by examiner

DEPTH CORRECTION BASED ON OPTICAL PATH MEASUREMENTS

BACKGROUND

Fiber-optic sensors have been utilized in a number of applications, and have been shown to have particular utility in sensing parameters in various environments. Optical fiber sensors can be incorporated into environments such as downhole environments and be used to sense various parameters of an environment and/or the components disposed therein, such as temperature, pressure, strain and vibration.

Parameter monitoring systems can be incorporated with downhole components as fiber-optic distributed sensing systems (DSS). Examples of DSS techniques include Optical Frequency Domain Reflectometry (OFDR), which includes interrogating an optical fiber sensor with an optical signal to generate reflected signals scattered from sensing locations (e.g., fiber Bragg gratings) in the optical fiber sensor.

Swept-wavelength interferometric-based sensing systems, frequently used for distributed fiber-optic sensing, are so-called because they rely upon interferometry to encode the sensor information. In some applications, however, the sensing fiber (the fiber containing or consisting of the sensor(s)) is subject to variations in length. These variations can result in reduced measurement accuracy.

SUMMARY

According to one embodiment, an apparatus for estimating an environmental parameter is disclosed. The apparatus includes an optical fiber including at least one core configured to be optically coupled to a light source and transmit an interrogation signal, the at least one core including a plurality of fiber Bragg gratings (FBGs) distributed along a measurement length of the optical fiber and configured to reflect light, a detector configured to receive a reflected return signal including light reflected from one or more of the plurality of sensing locations and a processor. The processor is configured to: receive data describing the reflected return signal; compare the received data to expected data for a reflected return signal for the optical fiber; determine a shift in wavelength of light reflected for one or more of the plurality of FBGs based on the comparison; determine a change in a length of a dead zone of the optical fiber based on the comparison; estimate locations of two or more of the plurality of FBG's based on the shift in wavelength and the change in length of the dead zone; and based on the estimates, estimate the environmental parameter.

According to another embodiment, a method for estimating an environmental parameter is disclosed. The method includes: disposing an optical fiber in a borehole in an earth formation, optical fiber including at least one core configured to be optically coupled to a light source and transmit an interrogation signal, the at least one core including a plurality of fiber Bragg gratings (FBGs) distributed along a measurement length of the optical fiber and configured to reflect light; transmitting a first interrogation signal into the optical fiber; receiving a reflected return signal including light reflected from one or more of the plurality of FBG's; receiving at a processor data describing the reflected return signal; comparing the received data to expected data for a reflected return signal for the optical fiber; determining a shift in wavelength of light reflected for one or more of the plurality of FBGs based on the comparison; determining a change in a length of a dead zone of the optical fiber based on the comparison; estimating locations of two or more of the plurality of FBG's based on the shift in wavelength and the change in length of the dead zone; and based on the estimates, estimating the environmental parameter.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

DETAILED DESCRIPTION

Figure 1:
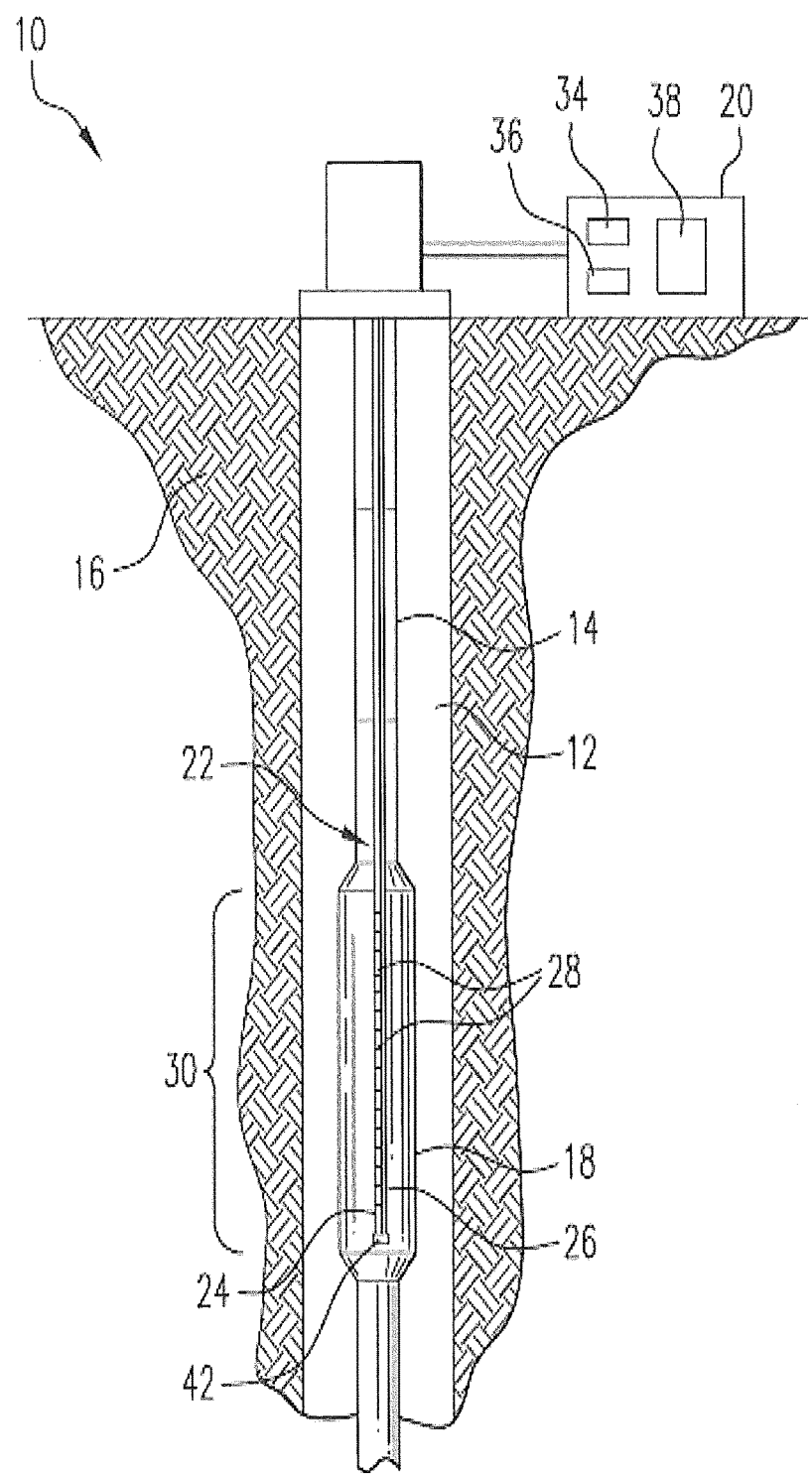
FIG. 1 illustrates an embodiment of a downhole drilling, monitoring, evaluation, exploration and/or production system.

Referring to FIG. 1, an exemplary embodiment of a downhole drilling, monitoring, evaluation, exploration and/or production system 10 disposed in a wellbore 12 is shown. A borehole string 14 is disposed in the wellbore 12, which penetrates at least one earth formation 16 for performing functions such as extracting matter from the formation and/or making measurements of properties of the formation 16 and/or the wellbore 12 downhole. The borehole string 14 is made from, for example, a pipe, multiple pipe sections or flexible tubing. The system 10 and/or the borehole string 14 include any number of downhole tools 18 for various processes including drilling, hydrocarbon production, and measuring one or more physical quantities in or around a borehole. Various measurement tools 18 may be incorporated into the system 10 to affect measurement regimes such as wireline measurement applications or logging-while-drilling (LWD) applications.

In one embodiment, a parameter measurement system is included as part of the system 10 and is configured to measure or estimate various downhole parameters of the formation 16, the borehole 14, the tool 18 and/or other downhole components. The measurement system includes an optical interrogator or measurement unit 20 connected in operable communication with at least one optical fiber sensing assembly 22. The measurement unit 20 may be located, for example, at a surface location, a subsea location and/or a surface location on a marine well platform or a marine craft. The measurement unit 20 may also be incorporated with the borehole string 12 or tool 18, or otherwise disposed downhole as desired.

An optical fiber assembly 22 is operably connected to the measurement unit 20 and is configured to be disposed downhole. The optical fiber assembly 22 includes at least one optical fiber core 24 (referred to as a "sensor core" 24) configured to take a distributed measurement of a downhole parameter (e.g., temperature, pressure, stress, strain and others). In one embodiment, the system may optionally include at least one optical fiber core 26 (referred to as a "system reference core" 26) configured to generate a reference signal. The sensor core 24 includes one or more sensing locations 28 disposed along a length of the sensor core, which are configured to reflect and/or scatter optical interrogation signals transmitted by the measurement unit 20. Examples of sensing locations 28 include fibre Bragg gratings, Fabry-Perot cavities, partially reflecting mirrors, and locations of intrinsic scattering such as Rayleigh scattering, and Brillouin scattering locations. If included, the system reference core 26 may be disposed in a fixed relationship to the sensor core 24 and provides a reference optical path having an effective cavity length that is stable relative to the optical path cavity length of the sensor core 24.

In one embodiment, a length of the optical fiber assembly 22 defines a measurement region 30 along which distributed parameter measurements may be taken. For example, the measurement region 30 extends along a length of the assembly that includes sensor core sensing locations 28.

The measurement unit 20 includes, for example, one or more electromagnetic signal sources 34 such as a tunable light source, a LED and/or a laser, and one or more signal detectors 36 (e.g., photodiodes). Signal processing electronics may also be included in the measurement unit 20, for combining reflected signals and/or processing the signals. In one embodiment, a processing unit 38 is in operable communication with the signal source 34 and the detector 36 and is configured to control the source 34, receive reflected signal data from the detector 36 and/or process reflected signal data.

In one embodiment, the measurement system is configured as a coherent optical frequency-domain reflectometry (OFDR) system. In this embodiment, the source 34 includes a continuously tunable laser that is used to spectrally interrogate the optical fiber sensing assembly 22. In one embodiment, the interrogation signal has a wavelength or frequency that is modulated or swept (e.g., linearly) over a selected wavelength or frequency range that includes a center frequency. Scattered signals reflected from intrinsic scattering locations, sensing locations 28 and other reflecting surfaces in the optical fiber assembly 22 may be detected, demodulated, and analyzed. Each scattered signal can be correlated with a location by, for example, a mathematical transform or interferometrically analyzing the scattered signals in comparison with a selected common reflection location. Each scattered signal can be integrated to reconstruct the total length and/or shape of the cable. A modulator (e.g., function generator) in optical communication with the tunable optical source 34 may be provided that modulates the optical source 34, such as by power, intensity or amplitude, using a modulation signal.

One term quite often used in such measurements is the optical path length (OPL) and refers to the distance traveled by light to sensing locations 28 and back. In the following examples it shall be understood that the sensing location is a fiber Bragg Grating (FBG).

Figure 2:
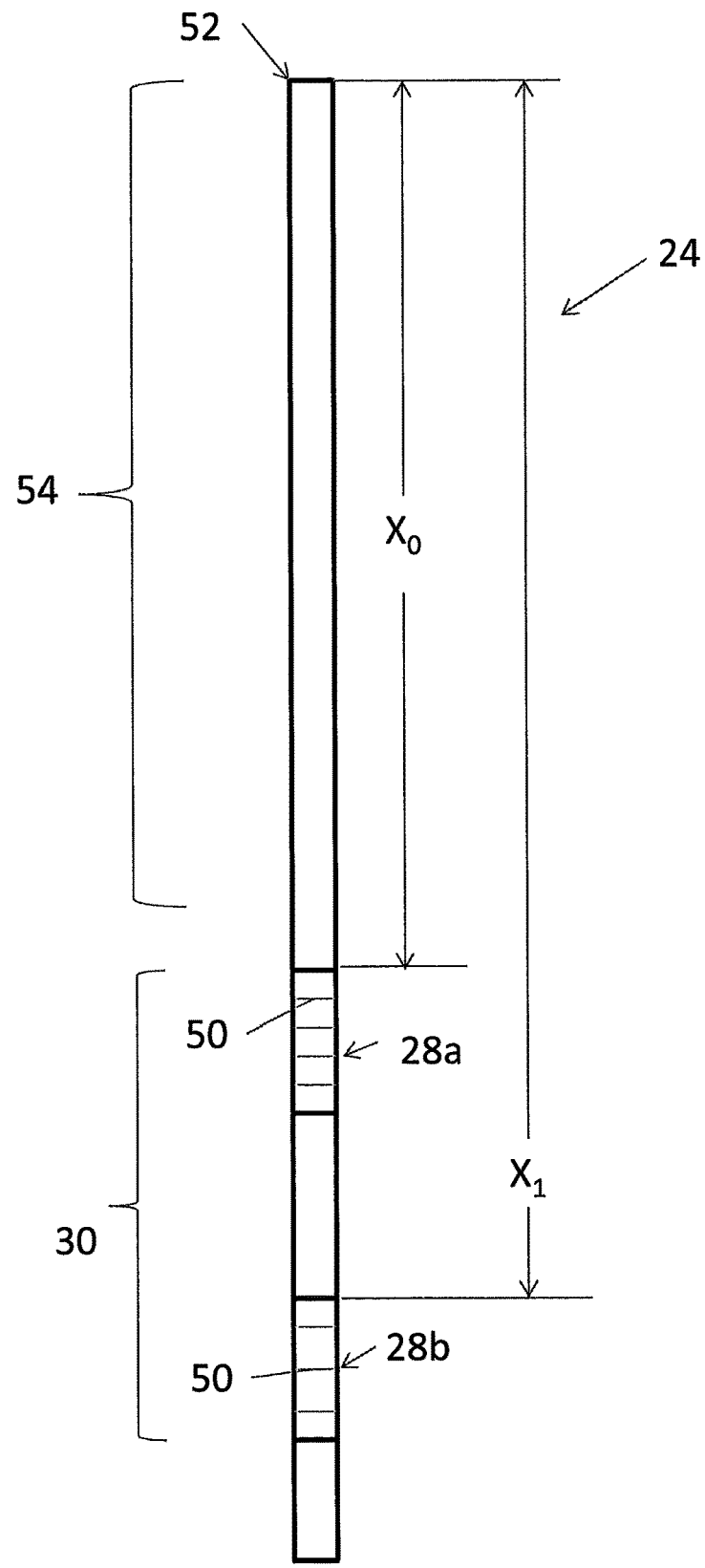
FIG. 2 illustrates an embodiment of a portion of a fiber according to one embodiment.

FIG. 2 shows a simplified example of a sensor core 24 that includes a measurement region 30. The sensor core 24 is also referred to as an optical fiber from time to time herein. The measurement region 30 in the illustrated example includes two sensing locations 28a and 28b that are implemented as FBG's. It shall be understood that the number of FBG's is not limited to two and the teachings herein may be applied to any sensor core having one or more FBG's. As is known in the art, an FBG consists of a periodic grating structure 50. Based on the period of the gratings, each FBG will reflect a particular wavelength(s) of light and transmits all others.

The sensor core 24 has a first end 52 that could be located, for example, at the source 34 (FIG. 1). The sensor core 24 extends from the first end 52 to the first FBG 28a. This section, in one embodiment, does not include any FBGs. The length of this section is denoted as $X_0$, and the section may be referred to as a "dead zone" from time to time herein and is given the reference numeral 54. Similarly, the length from the first end 52 to the second FBG 28b is denoted at $X_1$. Any subsequent FBG would include a length $X_Y$ from the first end to it. When a core 24 is first made the distances $X_0$ and $X_1$ are known. In addition, the wavelengths that will be reflected by the first and second FGBs 28a, 28b are also known. The known lengths/distances shall be referred to as "ideal spacings" and the known reflected wavelength(s) for a particular FBG shall be referred to herein as the "initial wavelength(s)" for that FBG.

During operation, the ideal spacings (e.g., $X_0$ and $X_1$) in the fiber 24 and/or the absolute wavelengths of the FBG's 28a, 28b change due to the imposition of external environmental factors such as heat, strain, and pressure, for example. These variations may cause variations in any measurement derived from the reflected wavelengths as such measurements may rely on one or both of the ideal spacings and initial wavelengths.

Figure 3:
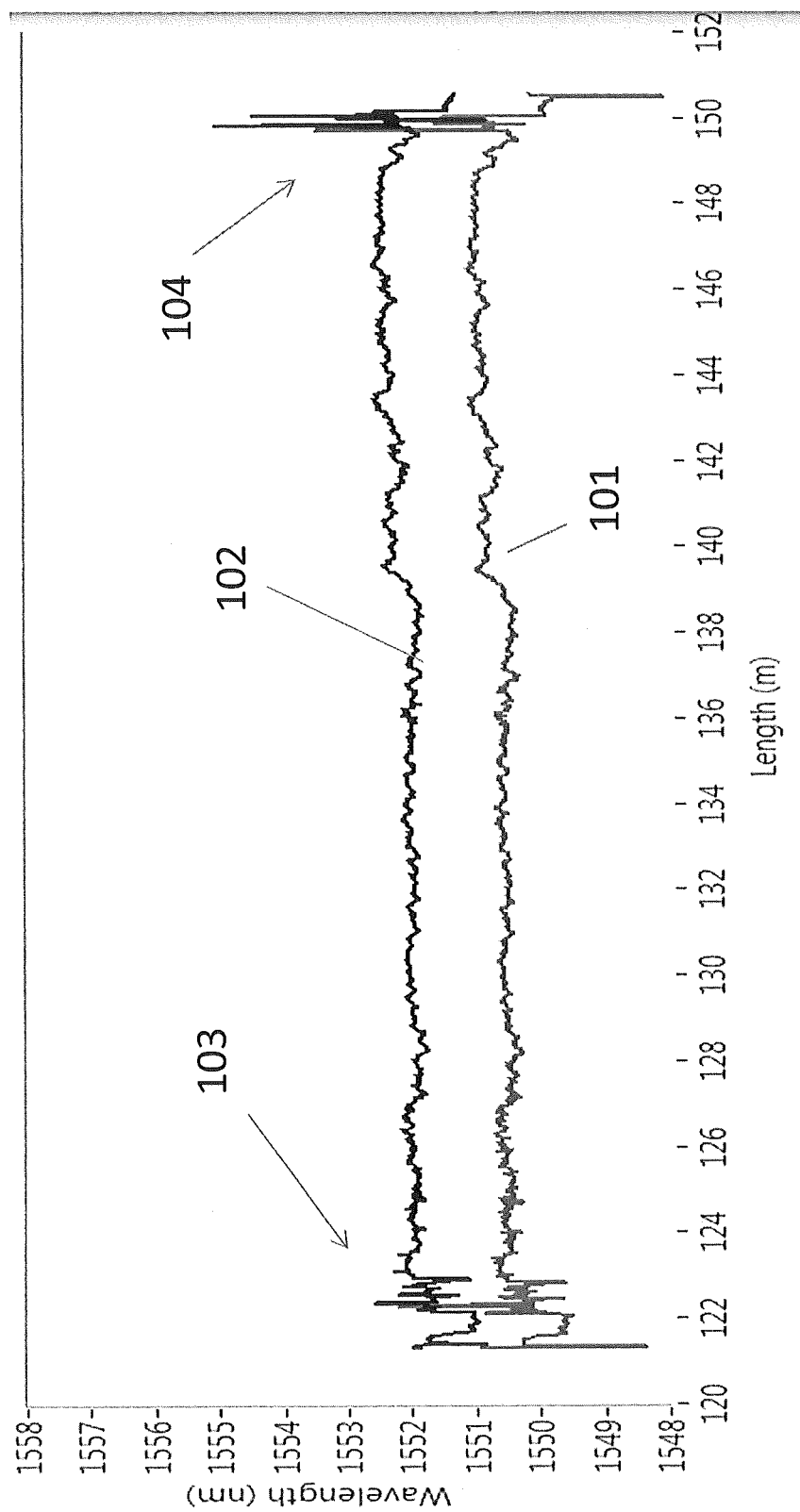
FIG. 3 shows a graph of expected versus return light received from a fiber such as the one illustrated in FIG. 3.

With reference to FIG. 3, two different traces 101, 102 are shown. The description for FIG. 3 (as well as other graphs herein) will refer back to the core 24 shown in FIG. 2 from time to time. These traces illustrate data formed from light reflected back to the first end 52 after an interrogation signal is transmitted into the core. The manner in which the data is formed is known in the art. The Y axis in the FIG. 3 is initial wavelength and the X axis is a distance from the first end. The first trace 101 shows a baseline or expected response of the core 24. The first trace 101 can be based off of data collected during actual testing or a computer generated model. In one embodiment, the data is generated before the core 24 is disposed in a borehole (e.g., a laboratory based test or a test performed at a job site). The second trace 102 shows an example of an actual response that may be created from data collected when the core is exposed to an external factor such as, for example, an increased temperature Of course, the external factor could be others factors such as strain from a load attached to the core. The data could be collected, for example, in a laboratory setting or while the core is disposed in a borehole. It shall be understood that while the description herein includes several graphs, such graphs are not required to practice the teachings herein and are presented for clarity of description only. Further, while units are given in regarding the axes of the illustrative graphs, those units are in no way limiting and are for example only.

In FIG. 3, the dead zone has an ideal spacing (e.g. $X_0$) of approximately 121 meters as can be determined from examination of the first trace 101. In particular, it can be assumed that no appreciable amount of light was reflected at any distance in the core 24 and, as such, the reflections begin at first FBG as indicted by the change in wavelengths shown in 121 meters. Further, trace 101 indicates that the ideal spacing of $X_1$ is approximately 150 meters.

The difference in received wavelengths between the traces 101 and 102 indicates that core 24, when under the external stress, reflects light having a wavelength approximately 1.5 nm greater than expected. This is due the fact that the external factor(s) have caused the individual gratings to move further apart (i.e. increasing the grating period) and, thus, shift the reflected wavelengths up from what is expected. In FIG. 3, it appears that the shift in wavelength of both the responses 103, 104 related to the first and second FBG's 28a, 28b, respectively in the illustrated example, is relatively the same. Of course, in some instances the difference in shift between actual and expected values could be different for each FBG.

Figure 4A:
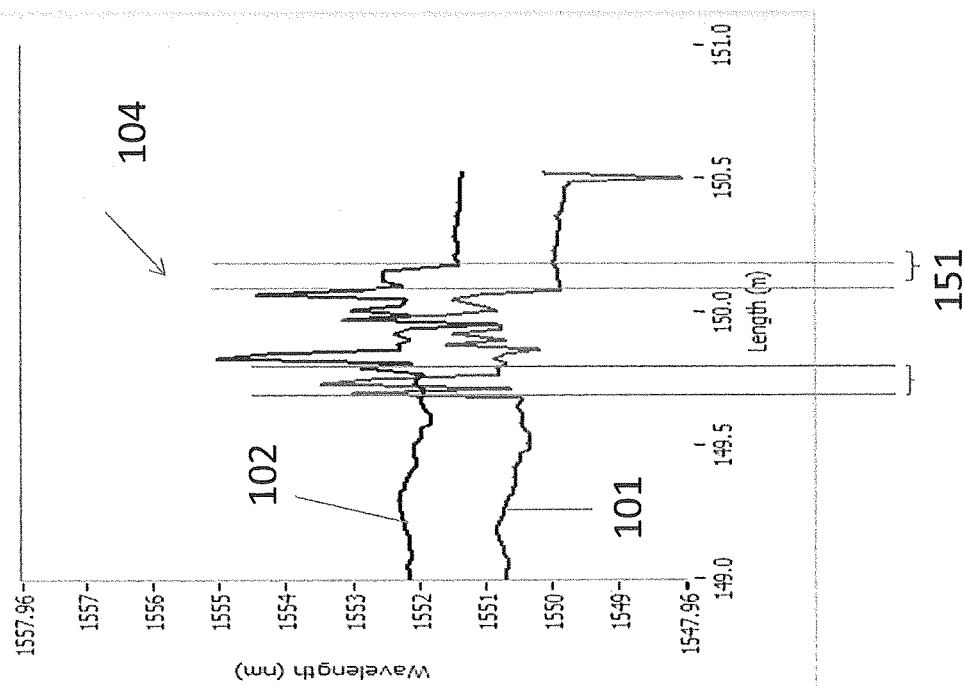
FIGS. 4A and 4B, respectively, show enlarged portions of the graph shown in FIG. 3.
Figure 4B:
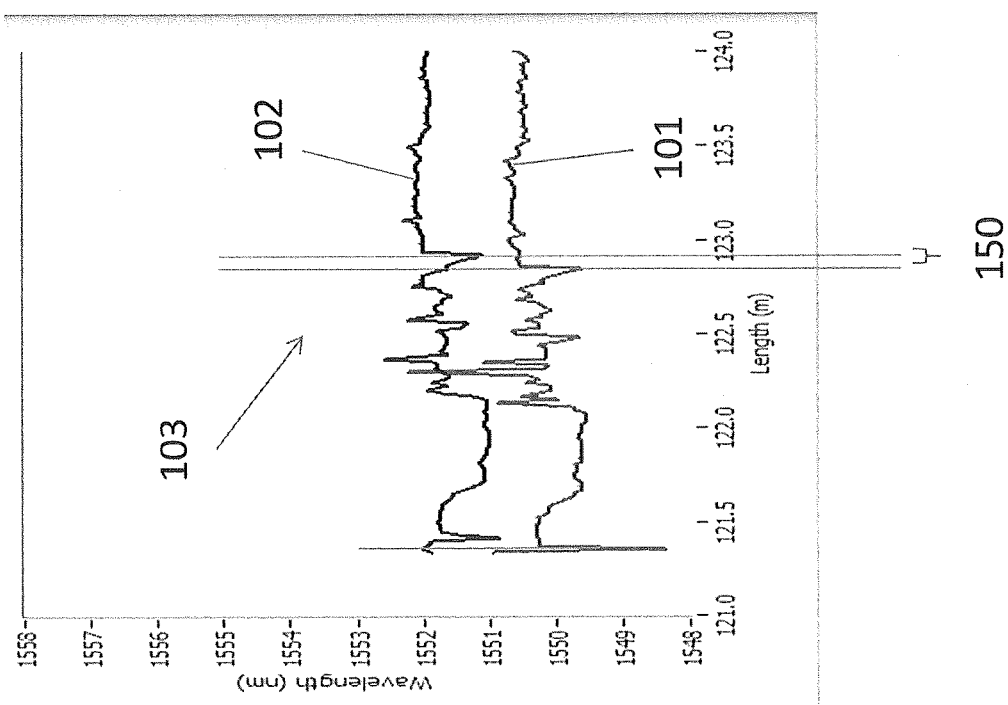

FIGS. 4A and 4B, respectively, show enlarged portions of the graph shown in FIG. 3 in regions near responses 103 and 104. In these enlarged FIGS. the shift in the each of the location of first and second FBGs 28a and 28b, respectively, are illustrated as the shifts labelled 150 and 151 between similar locations in the traces 101 and 102. Of course, the shifts could be determined without the use a graph by using, for example, numerical techniques. In more detail, shift 150 represents the difference between the measured and expected values of $X_0$ and shift 151 represents the difference between the measured and expected values of $X_1$.

In the above examples, the shift in location of only one grating is illustrated. It shall be understood that not only do variations in $X_0$ and $X_1$ affect the locations of the grating, but also, changes in the fiber between the individual gratings can affect the location of each of the gratings. As such, in one embodiment, for each grating a new location is determined. In one embodiment, the expected locations of a particular FBG can be determined based on the following formula:

$$X_N = X_0 + K \sum_{i=1}^{N} \frac{\Delta \lambda_i}{\lambda_0} \Delta X$$

where N is the number of the current FBG (starting at 1 for the first FBG), K is a constant (1 in most cases), $X_0$ is the location of the first FBG, $\lambda_0$ is the center of a wavelength scan, is the difference between the measured and initial reflected wavelength for a particular FBG, and $\Delta X$ is spacing (ideal) between each grating. Thus, given the value $X_0$, determined as shown above and below, and the shift between the initial versus actual reflected wavelengths, the location of each grating may be estimated with greater accuracy. When such estimates are known, more accurate measurements may be computed by the processing unit 38 (FIG. 1). How such measurements are made based on the reflected light is well known and not discussed further herein.

Figure 5:
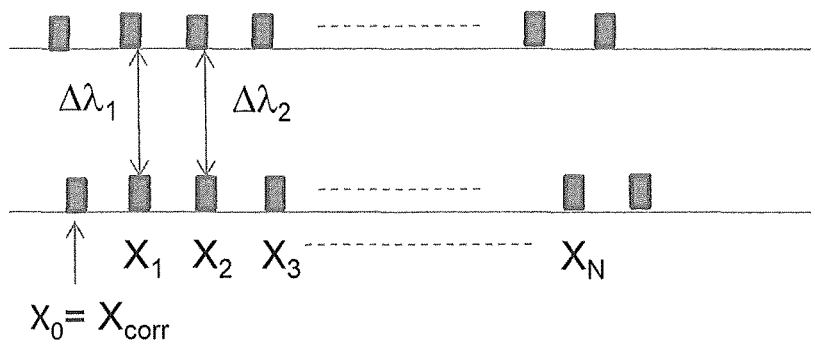
FIG. 5 shows an example of baseline and actual responses used in an autocorrelation procedure.

With reference now to FIG. 5, an example of how to form a corrected value of $X_0$ is disclosed. A current scan 503 taken while the core is disposed in a borehole is compared to a baseline scan 501. Each of the responses form the FBG's are lined up. This ensures that $X_0$ on the current scan 503 is lined up with $X_0$ on the baseline scan 501. In this manner, the location of the first FBG ($X_0$) in the above equation can be replaced with the location of the first FBG in the current scan ($X_{corr}$). The above procedure may be referred to as an autocorrelation procedure herein.

From the above description it shall be understood that systems for performing measurements, methods of forming measurements and methods of calibrating the measurement fiber have been disclosed. Further, it shall be understood that according to one embodiment, a method of forming a measurement can include disposing an optical fiber in a borehole in an earth formation. The optical fiber includes at least one core configured to be optically coupled to a light source and transmit an interrogation signal, the at least one core includes a plurality of fiber Bragg gratings (FDGs) distributed along a measurement length of the optical fiber and configured to reflect light. The method also includes: transmitting a first interrogation signal into the optical fiber; receiving a reflected return signal including light reflected from one or more of the plurality of sensing locations; receiving at a processor data describing the reflected return signal; comparing the received data to expected data for a reflected return signal for the optical fiber; determining a shift in wavelength of light reflected for one or more of the plurality of FBGs based on the comparison; determining a change in a length of a dead zone of the optical fiber based on the comparison; estimating locations of individual gratings of the one or more of the plurality of FBG's based on the shift in wavelength and the change in length of the dead zone; and based on the estimates, estimating the environmental parameter.

The optical fiber assembly 22 and/or the measurement system are not limited to the embodiments described herein, and may be disposed with any suitable carrier. The measurement system, optical fiber assembly 22, the borehole string 14 and/or the tool 18 may be embodied with any suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, bottom-hole assemblies, and drill strings.

In support of the teachings herein, various analysis components may be used, including a digital and/or an analog system. Components of the system, such as the measurement unit 20, the processor 38, the processing assembly 50 and other components of the system 10, may have components such as a processor, storage media, memory, input, output, communications link, user interfaces, software programs, signal processors (digital or analog) and other such components (such as resistors, capacitors, inductors and others) to provide for operation and analyses of the apparatus and methods disclosed herein in any of several manners well appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling unit, heating unit, motive force (such as a translational force, propulsional force or a rotational force), magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

It will be recognized that the various components or technologies may provide certain necessary or beneficial functionality or features. Accordingly, these functions and features as may be needed in support of the appended claims and variations thereof are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating an environmental parameter, the apparatus comprising:
    a light source that provides a swept interrogation signal that is swept over a selected frequency range;
    an optical fiber including at least one core configured to be optically coupled to the light source and transmit the swept interrogation signal, the at least one core including a plurality of fiber Bragg gratings (FBGs) distributed along a measurement length of the optical fiber and configured to reflect light;
    a detector configured to receive a reflected return signal including light reflected from the swept interrogation signal by one or more of the plurality of sensing locations; and
    a processor, the processor configured to:
        receive data describing the reflected return signal while the detector is in a borehole;
        compare the received data to expected data for a reflected return signal for the optical fiber;
        determine a shift in wavelength of light reflected for one or more of the plurality of FBGs based on the comparison;
        determine a change in a length of a dead zone of the optical fiber based on the comparison;
        estimate locations of two or more of the plurality of FBG's based on the shift in wavelength and the change in length of the dead zone; and
        based on the estimates, estimate the environmental parameter.

2. The apparatus of claim 1, wherein the expected data is formed based on a test of the optical fiber in a first condition and the reflected signal is received when the optical fiber is in a second condition, different than the first condition.

3. The apparatus of claim 2, wherein the second condition includes exposure to downhole conditions.

4. The apparatus of claim 1, wherein determining the shift includes determining a wavelength of light reflected from a first of the plurality of FBG's.

5. The apparatus of claim 4, wherein determining the shift includes determining a wavelength of light reflected from a second of the plurality of FBG's.

6. The apparatus of claim 1, wherein the dead zone ends at a first of the plurality of FBG's.

7. The apparatus of claim 6, wherein determining a change in the length of the dead zone includes determining a location of a beginning or end of the first of the plurality of FBG's.

8. The apparatus of claim 1, wherein estimating locations of individual gratings includes solving $$X_N = X_0 + K \sum_{i=1}^{N} \frac{\Delta \lambda_i}{\lambda_0} \Delta X$$

where N is the number of the current FBG, K is a constant, $X_0$ is the location of the first FBG, $\lambda_0$ is the center of a wavelength scan, $\Delta \lambda_i$ is the difference between the measured and initial reflected wavelength for a particular FBG, and $\Delta X$ is spacing between each grating.

9. The apparatus of claim 8, wherein an autocorrelation procedure is used to form the value of $X_0$.

10. The apparatus of claim 1, wherein the one or more environmental parameter is selected from at least one of temperature, pressure, and strain.

11. The apparatus of claim 1, wherein the light source is configured to emit a coherent swept-wavelength interrogation signal.

12. A method for estimating an environmental parameter, the method comprising:
    disposing an optical fiber in a borehole in an earth formation, optical fiber including at least one core configured to be optically coupled to a light source and transmit an interrogation signal, the at least one core including a plurality of fiber Bragg gratings (FBGs) distributed along a measurement length of the optical fiber and configured to reflect light;
    transmitting a first swept interrogation signal into the optical fiber, the first swept interrogation signal being swept over a selected frequency range while the optical fiber is in the borehole;
    receiving a reflected return signal including light reflected from one or more of the plurality of FBG's;
    receiving at a processor data describing the reflected return signal;
    comparing the received data to expected data for a reflected return signal for the optical fiber;
    determining a shift in wavelength of light reflected for one or more of the plurality of FBGs based on the comparison;
    determining a change in a length of a dead zone of the optical fiber based on the comparison;
    estimating locations of two or more of the plurality of FBG's based on the shift in wavelength and the change in length of the dead zone; and
    based on the estimates, estimating the environmental parameter.

13. The method of claim 12, wherein the expected data is formed based on a test of the optical fiber in a first condition and the reflected signal is received when the optical fiber is exposed to downhole conditions.

14. The method of claim 12, wherein determining the shift includes determining a wavelength of light reflected from a first of the plurality of FBG's.

15. The method of claim 14, wherein determining the shift includes determining a wavelength of light reflected from a second of the plurality of FBG's.

16. The method of claim 12, wherein the dead zone ends at a first of the plurality of FBG's.

17. The method of claim 16, wherein determining a change in the length of the dead zone includes determining a location of a beginning or end of the first of the plurality of FBG's.

18. The method of claim 12, wherein estimating locations of individual gratings includes solving $$X_N = X_0 + K \sum_{i=1}^{N} \frac{\Delta \lambda_i}{\lambda_0} \Delta X$$

where N is the number of the current FBG, K is a constant, $X_0$ is the location of the first FBG, $X_0$ is the center of a wavelength scan, $\lambda\lambda_i$ is the difference between the measured and initial reflected wavelength for a particular FBG, and $\Delta X$ is spacing between each grating.

\* \* \* \* \*